United States Patent [19]

Gras et al.

[11] 4,306,051
[45] * Dec. 15, 1981

[54] ISOCYANURATE GROUP-AND TERMINALLY BLOCKED ISOCYANATE GROUP-CONTAINING COMPOUNDS

[75] Inventors: Rainer Gras; Elmar Wolf, both of Herne, Fed. Rep. of Germany

[73] Assignee: Chemische Werke Huls AG, Recklinghausen, Fed. Rep. of Germany

[*] Notice: The portion of the term of this patent subsequent to Jan. 20, 1998, has been disclaimed.

[21] Appl. No.: 135,187

[22] Filed: Mar. 28, 1980

Related U.S. Application Data

[63] Continuation of Ser. No. 926,314, Jul. 20, 1978, which is a continuation-in-part of Ser. No. 889,217, Mar. 23, 1978, abandoned.

[30] Foreign Application Priority Data

Jul. 20, 1977 [DE] Fed. Rep. of Germany ....... 2732622

[51] Int. Cl.$^3$ ...................... C08G 18/80; C08G 18/79
[52] U.S. Cl. ...................................... 528/45; 252/182; 528/67; 544/193; 544/222
[58] Field of Search .................. 528/45, 67; 252/182; 544/193, 222

[56] References Cited

U.S. PATENT DOCUMENTS

| | | | |
|---|---|---|---|
| 2,952,665 | 9/1960 | Bunge et al. | 528/45 |
| 3,577,391 | 5/1971 | Argabright et al. | 528/45 |
| 3,676,402 | 7/1972 | MaBui et al. | 528/45 |
| 3,691,134 | 9/1972 | Feldman et al. | 260/77.5 AT |
| 3,822,240 | 7/1974 | Schmitt et al. | 528/45 |
| 3,893,977 | 7/1975 | Wingler | 528/45 |
| 3,919,218 | 11/1975 | Schmitt et al. | 544/222 |
| 4,088,637 | 5/1978 | Zecher et al. | 528/45 |

Primary Examiner—H. S. Cockeram
Attorney, Agent, or Firm—Oblon, Fisher, Spivak, McClelland & Maier

[57] ABSTRACT

A method for the production of blocked isocyanate- and isocyanurate group-containing compounds which comprises reacting a monomeric cycloaliphatic polyisocyanate to form an intermediate mixture comprising an isocyanurate containing at least two free isocyanate groups; and blocking the intermediate isocyanurate mixture with dimethylketoxime at 50°–120° C., wherein the amount of said dimethylketoxime is such that one equivalent of NCO group reacts with one equivalent of the dimethylketoxime. A mixture containing isocyanurate and blocked isocyanate groups which comprises at least 10% by weight of a cycloaliphatic isocyanurate containing at least two isocyanate groups blocked with dimethylketoxime and a monomeric polyisocyanate blocked with dimethylketoxime in such amounts as necessary to complete 100% by weight of the mixture, and wherein the unblocked NCO-group content of the monomeric polyisocyanate is less than 0.5% by weight.

17 Claims, 4 Drawing Figures

ISOCYANURATE GROUP- AND TERMINALLY BLOCKED ISOCYANATE GROUP-CONTAINING COMPOUNDS

BACKGROUND OF THE INVENTION

Reference to prior applications.

This application is a Continuation of application Ser. No. 926,314 filed July 20, 1978 which is a Continuation-in-Part of application Ser. No. 889,217 filed on Mar. 23, 1978 and now abandoned.

Field of the Invention

The present invention relates to a method for the production of new compounds with adjusted isocyanurate group content, as well as the compounds obtainable by this method.

Description of the Prior Art

The production of masked isocyanates, also called isocyanate yielders, is known and is described in Houben-Weyl, Methoden des organischen Chemie XIV/2 pp. 61–70. Blocking agents known are tertiary alcohols, phenols, acetoacetic ester, malonic ester, acetylacetone, phthalimide, imidazole, hydrogen, chloride, hydrogen cyanide and ε-caprolactam.

These masked isocyanates possess the property of reacting like isocyanates at elevated temperature. The splitting occurs easier the more acid the H-atom of the masking group is. Such blocked isocyanates are described in DT-CS 21 66 432. Also, terminally blocked isocyanates, which contain in addition uretdione groups, have been described in DT-OS 25 02 934.

Surprisingly there are no references in the literature to aliphatic polyisocyanates exhibiting isocyanurate groups and terminally blocked isocyanate groups. To be sure, blocked aromatic isocyanurates for producing heat-resistant adherent urethane bake-on lacquers, especially for electric wire insulation in a JA-A5 73,30453, filed Dec. 24, 1969, have been proposed. The production of aliphatic polyisocyanates containing such blocked isocyanurate groups is, however, still unknown.

SUMMARY OF THE INVENTION

Object of the invention is a method for production of blocked isocyanate group- and isocyanurate group-containing compounds of aliphatic and/or cycloaliphatic polyisocyanates and monofunctional, acid hydrogen-containing blocking agents, wherein that one first converts the aliphatic and/or cycloaliphatic polyisocyanate(s) in known manner into a mixture consisting of an isocyanurate containing at least 2 free isocyanate groups and then transforms this intermediate product with dimethylketoxime as monofunctional, acid hydrogen-containing blocking agent at 50°–120° C., wherein the dimethylketoxime is introduced in such quantities that to an NCO group-equivalent there corresponds an equivalent of dimethylketoxime. A variant consists of first freeing the resultant intermediate product of monomeric polyisocyanate and then blocking the practically monomer-free polyisocyanate in the described manner.

Another object of the invention, is to describe compounds which are blocked isocyanate group- and isocyanurate group-containing compounds consisting of at least 10 wt% of a dimethylketoxime-blocked isocyanurate containing at least 2 isocyanate groups before the blocking and if necessary, a quantity, making up the rest of the 100 wt%, of a dimethylketoxime-blocked, monomeric polyisocyanate with a content of unblocked NCO groups of <0.5 wt%.

BRIEF DESCRIPTION OF THE DRAWINGS

A more complete appreciation of the invention and many of the attendant advantages thereof will be readily obtained as the same becomes understood by reference to the following detailed description when considered in connection with the accompanying drawings wherein.

DETAILED DESCRIPTION OF THE PREFERRED EMBODIMENTS

Figure 1:
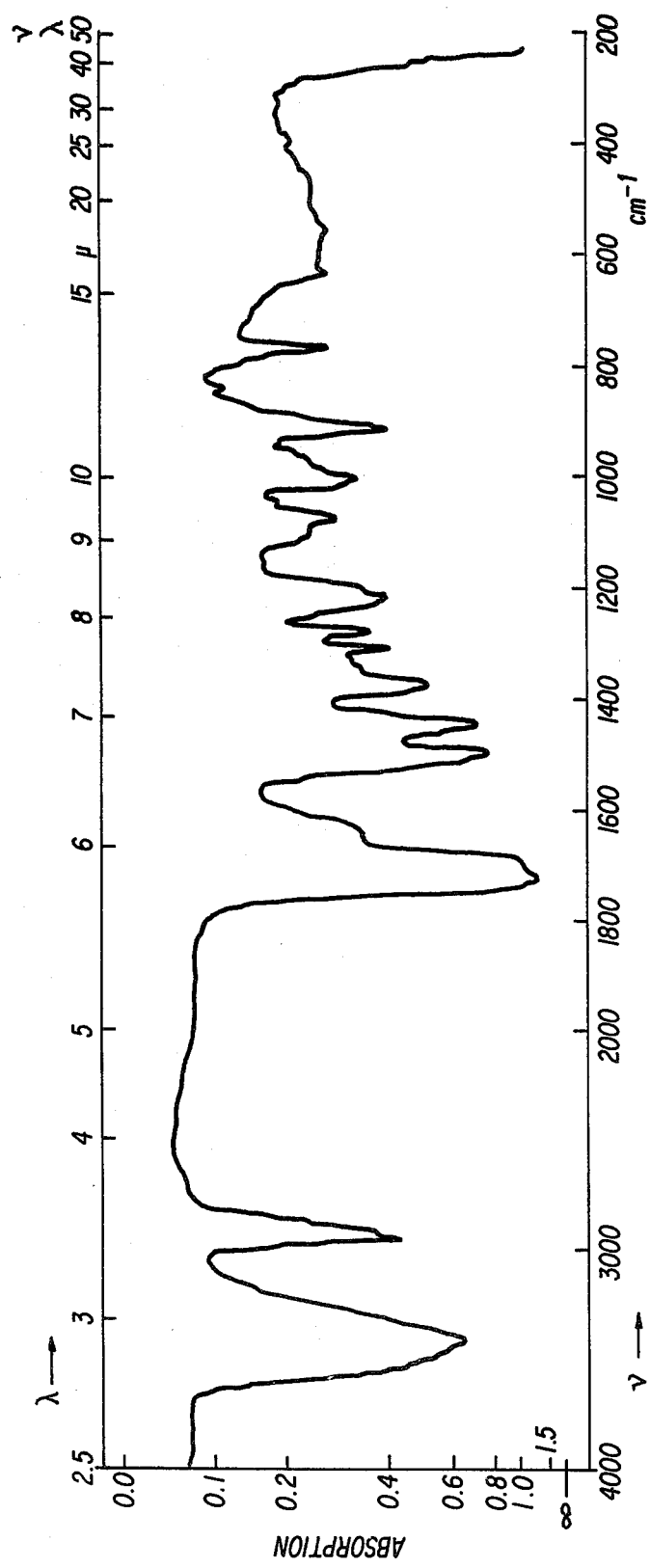
FIG. 1 is the infrared spectrum of the reaction product of Example 1B.

The monomeric polyisocyanate may conveniently be identical with that used for production of the isocyanurate. Especially preferred as monomeric polyisocyanate, on account of its good optical qualities, is 3-isocyanatomethyl-3,5,5-trimethyl-cyclohexylisocyanate and as isocyanurate, the addition product derived from it. The isocyanurate can also be a mixture of the trimer and higher addition product of the monomer polyisocyanate. The isocyanurate group content of the compounds produced according to the invention amounts to 2–8 wt%.

Suited for production of the isocyanuratoisocyanates, i.e., for trimerization, are for example polyisocyanates, in particular diisocyanates, such as aliphatic, cycloaliphatic and/or araliphatic, i.e., aryl-substituted aliphatic diisocyanates, as described for example in the article by W. Siefken in Justus Liebis's Annalen des Chemie 562. pp. 75–136, like 1,2-ethylenediisocyanate, 1,4-tetramethylenediisocyanate, 1,6-hexamethylenediisocyanate, 2,2,5-or 2,4,4-trimethyl-1,6-hexamethylenediisocyanate (TMDI), 1,12-dodecanediisocyanate, ω,ω'-diisocyanatodipropylether, cyclobutane-1,2-diisocyanate, cyclohexane-1,3 and 1,4-diisocyanate, 3-isocyanatomethyl-3,5,5-trimethylcyclohexylisocyanate, which is also called isophoronediisocyanate and abbreviated as IPDI, hexahydro-1,2- or -1,4-phenylenediisocyanate, 2,4- and 2,6-hexahydrotoluylenediisocyanate, perhydro-2,4-and/or -4,4'-diphenylmethanediisocyanate, ω,ω'-diisocyanato-1,4-diethylbenzene as well as optional mixtures of these isomers. Other suitable isocyanates are described in the cited article in the Annalen on p. 122 ff.

Especially preferred, as a rule are the technically readily accessible aliphatic or cycloaliphatic diisocyanates, like 3-isocyanatomethyl-3,5,5-trimethyl-cyclohexylisocyanate, 2,4- and 2,5-hexahydrotoluylenediisocyanate, perhydro-2,4'- and/or -4,4'-diphenylmethanediisocyanate and 1,6-hexamethylenediisocyanate as well as their isomer mixtures.

In the trimerization of the polyisocyanates there can also be used to a limited extent aliphatic and/or cycloaliphatic monoisocyanates comparable with the above polyisocyanates, as long as the isocyanuratoisocyanate formed contains at least 2 free isocyanate groups on the average.

These starting materials for the method of the invention are then subjected in known manner to trimerization, as described for example in GB-PS 1 391 066 and DT-OS 23 25 826. The trimerization of the described aliphatic or cycloaliphatic isocyanates is a catalytic reaction. The catalysts used can be metal compounds from the group of salts and bases and homopolar metal compounds like metal naphthanates, Na-benzoate in DMF, alkaline earth-acetates, -formates and -carbonates, metal alkoxides, AlCl$_3$ and Fe-acetylacetonate. Particularly suited for the trimerization of aliphatic isocyanates is the proposed catalyst system of N,N′-endoethylenepiperazine and propylene oxide. The trimerization can be carried out neat or in inert organic solvents. In performing the trimerization process it is essential to interrupt the reaction at a certain isocyanate content of the mixture, and indeed preferably when 30–50% of the NCO groups under trimerization have reacted. The unconverted isocyanate is then separated from the isocyanurate formed through vacuum distillation.

In the method of the invention the thus available isocyanuratoisocyanate is used either as exclusively isocyanate components or in mixture with isocyanurate-free polyisocyanates. The addition of isocyanurate group-free polyisocyanates permits the properties of the products of the method, in particular their melting point, to be varied simply in the desired manner.

It is especially advantageous in the method of the invention to use as isocyanurate component the aforementioned in situ-produced triisocyanate mixture, which is available through partial trimerization of a suitable diisocyanate.

Once the thus-obtained polyisocyanates with isocyanurate groups, preferably triisocyanates, or their mixtures with isocyanurate group-free polyisocyanates, preferably diisocyanates are obtained, they are used as intermediates for the preparation of the products of the present invention.

In a further step in the method of the invention the products of the intermediate stage, as described below, are now converted, without further modification, into the product of the invention, exhibiting the isocyanurate groups and terminally-blocked isocyanate groups.

Dimethylketoxime has proved especially suitable for readily entering into an addition reaction with the isocyanate group-containing compounds at temperatures over 50° C., preferably between 80° and 120° C. The resultant addition products in the mixture react with nonvolatile primary polyols with hydroxyl groups at temperatures between 100° and 200° C. with liberation of dimethylketoxime with the nonvolatile polyols during urethane formation.

For carrying out the blocking reaction the isocyanate component is generally produced first and the blocking agent added thereto. The reaction can be carried out with or without the presence of a suitable (inert) solvent. The blocking reaction is generally carried out at 80°–120° C. The dimethylketoxime is introduced in such quantities that to an NCO group-equivalent there corresponds an equivalent of blocking agent. Also the usual isocyanate-polyaddition reaction accelerating catalysts, line tin(II)-octanoate can be used. The catalysts, as a rule, are introduced in an amount between 0.001 and 1 wt% depending on the quantity of active hydrogen containing-compounds which are reactive with isocyanates.

The products of the method of the invention, are in general compounds in the molecular weight range of 300–3000, preferably 400–2000. The products of the method have melting points or ranges of 30°–200° C., preferably 60°–170° C. The preferred polyisocyanates containing the invention's isocyanurate groups are characterized beyond that by a content of isocyanurate groups (calculated as (CO—N—)$_3$) of 2 wt% to 14 wt%, preferably 3–10 wt% and a content of terminally blocked isocyanate groups (calculated as NCO) of 2–18, preferably 10–17 wt%.

The compounds of the present invention are particularly suited, on account of their low melting points and simultaneously rather high molecular weights, as cocatalysts for the anionic polymerization of ε-caprolactam.

The products of the method are further suitable as hardeners for higher functional thermoplastic compounds which contain Zerewitinoff-active hydrogen atoms. In combination with such compounds containing Zerewitinoff-active hydrogen atoms, the products of the present invention form, above 120° C., preferably at 160°–200° C., systems which are hardenable to high-value plastics. The most important area of application for such systems is as binder for (PUR-) lacquer powders. The products of the method of the invention are also well suited for the production of single-component bakeon lacquers (especially for coil coating) which are stable upon storage.

Having generally described this invention, a further understanding can be obtained by reference to certain specific examples which are provided herein for purposes of illustration only and are not intended to be limiting unless otherwise specified.

EXAMPLE 1 z. Production of the Triisocyanurate 100 parts by weight of isophoronediisocyanate (IPDI) were heated with 0.5 parts by wt. of the catalyst system of 1,4-diazabicyclooctane-[2,2,2] (also called Dabco ®) and propylene oxide for 3 hours at 120° C. During this time the NCO content dropped from 37.8% (corresponding to 100% IPDI) to 28.3% (50% IPDI conversion). To deactivate the catalyst the reaction mixture was cooled to 40° C. and stripped at this temperature for ½ hour with nitrogen. This changed the NCO content of the reaction mixture only slightly to 28.2%.

b. Blocking of the triisocyanurate

To 100 parts by wt of this isocyanato-isocyanurate mixture at 100° C., 49 parts by wt. of dimethylketoxime were added a little at a time so that the reaction temperature did not go above 120° C. To complete the reaction the mixture was held at 120° C. for another 2 hours.

| Free NCO (%): | <0.6 |
| Blocked NCO (%): | 18.92 |
| Melting temperature: | 71–76° C. |
| Decomposition temperature: | ~160° C. |
| Glass transition Temperature (DTA): | 41–60° C. |

FIG. 1 gives the IR-spectrum of the reaction product.

EXAMPLE 2 a. Production of the Triisocyanurate 100 parts by wt. of IPDI were heated with 0.75 parts by wt. of a catalyst system as in Example 1a for 2 hours at 120° C. In this time the NCO content fell from 37.8% to 29.4%. To deactivate the catatyst the reaction mixture was subjected at 120° C. to a 30 Torr vacuum for 15 minutes. During this time the NCO content changed to 27%.

b. Blocking of the Triisocyanurate

To 100 parts by wt. of this isocyanato-isocyanurate mixture at 110° C. 46.9 parts by wt. of dimethylketoxime were added gradually so that the reaction temperature did not exceed 120° C. To carry the reaction to completion the mixture was held at 120° C. for another 2 hours.

| | |
|---|---|
| Free NCO (%): | <0.5 |
| Blocked NCO (%): | 18.38 |
| Melting Temperature: | 75–82° C. |
| Decomposition Temperature: | ~160° C. |
| Glass transition Temperature (DTA): | 50–69° C. |

Figure 2:
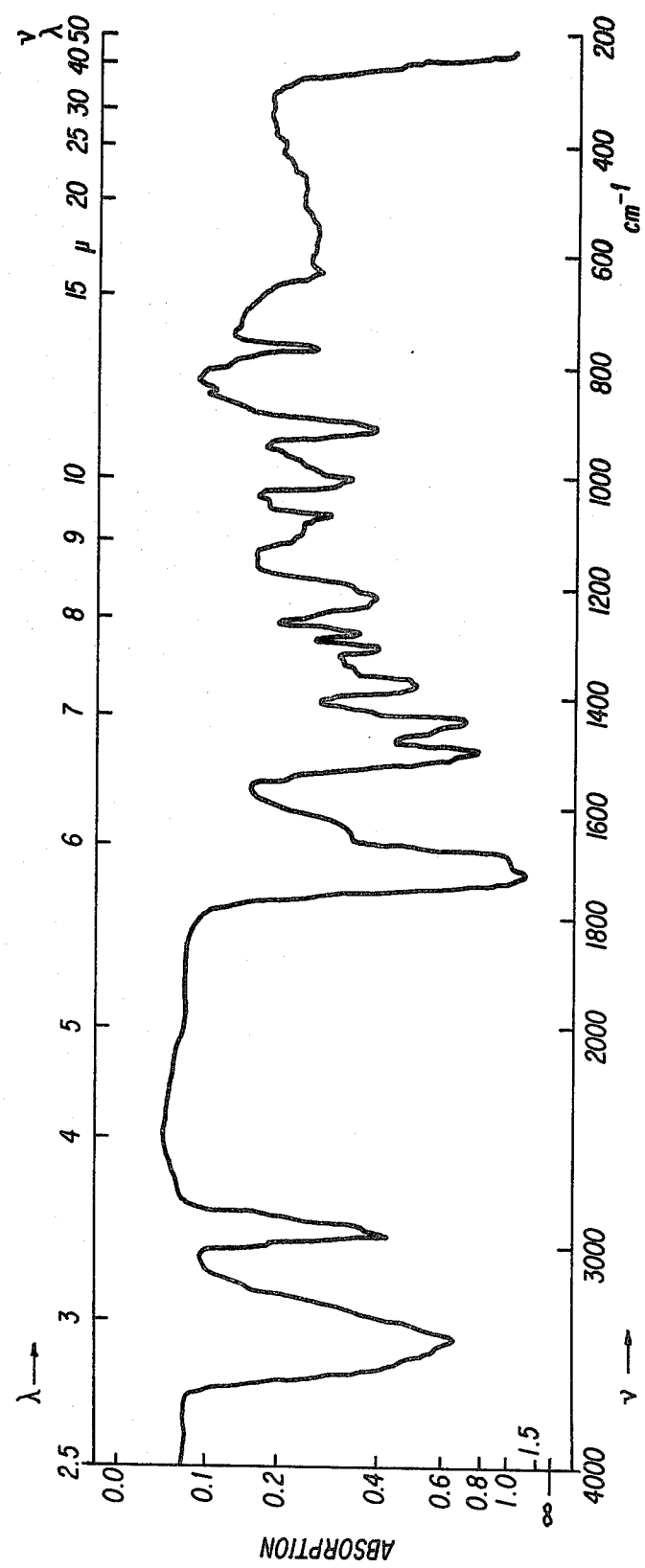
FIG. 2 shows the IR-spectrum of the reaction product from Example 2B.

FIG. 2 shows the IR-spectrum of the reaction mixture.

EXAMPLE 3 a. Production of the Triisocyanurate 100 parts by wt. of IPDI were heated with 0.5 parts by wt. of the catalyst described in Example 1a for 4.5 hours at 120° C. The progress of the trimerization was followed by means of the index of refraction, viscosity or NCO content. At an NCO content of 25.8% a 20 Torr vacuum was maintained for half an hour. After cooling, the reaction mixture had an NCO content of 25%.

b. Blocking of the Triisocyanurate

To 100 parts by wt. of this isocyanatoisocyanurate mixture at 120° c. 43.4 parts by wt. of dimethylketoxime were slowly added with thorough stirring. After addition of all the dimethylketoxime the reaction mixture was heated for another hour to 130° C.

| | |
|---|---|
| Free NCO (%): | <0.6 |
| Blocked NCO (%): | 17.42 |
| Melting Temperature: | 85–89° C. |
| Decomposition Temperature: | 160° C. |
| Glass Transition Temperature (DTA): | 51–62° C. |

Figure 3:
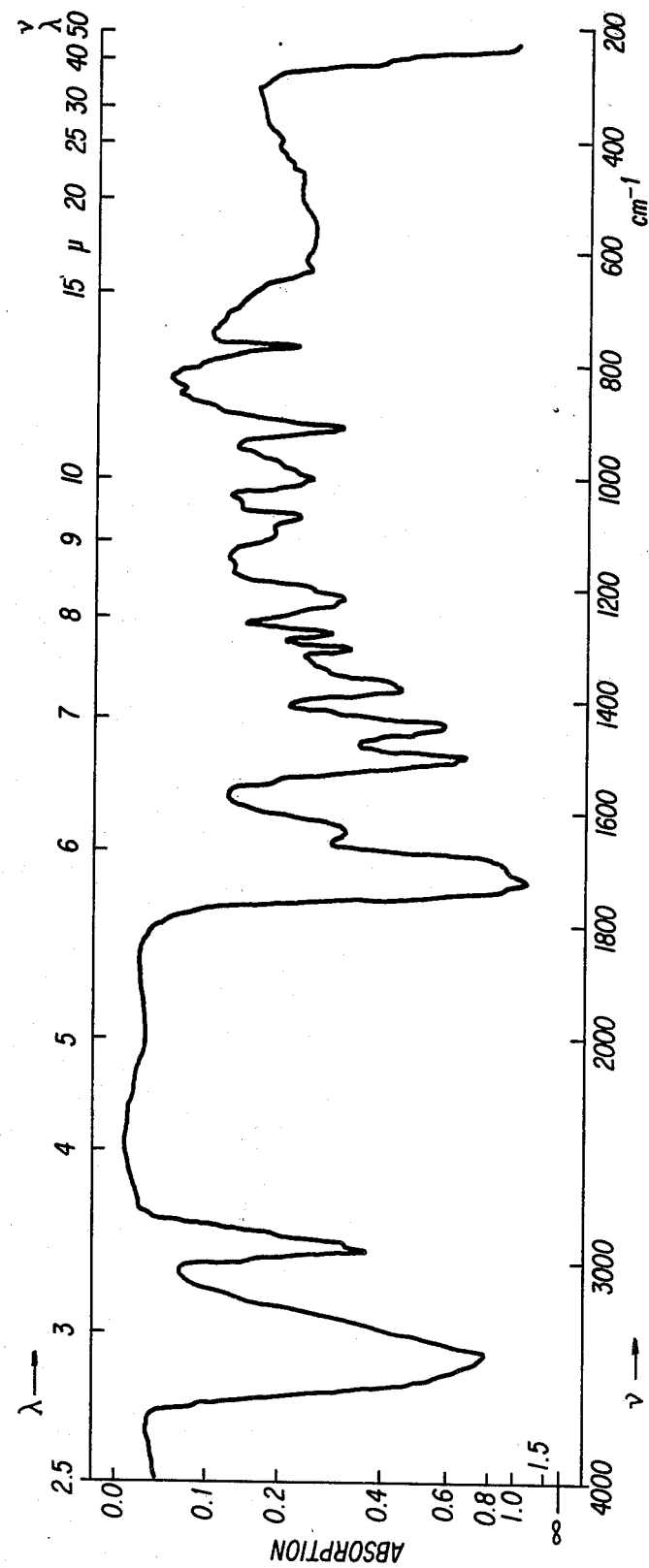
FIG. 3 shows the IR-spectrum of the reaction product from Example 3B.

The IR-spectrum of the reaction product is given in FIG. 3.

EXAMPLE 4 a. Production of the Triisocyanurate

By the method described in 1a–3a there was produced from IPDI an isocyanatoisocyanurate mixture (with deactivated cat.) with an NCO content of 20.9%.

b. Blocking of the Triisocyanurate

To 100 parts by wt. of this mixture (NCO: 20.9%) at 140° C. 36.3 parts by wt. of dimethylketoxime were added with intensive stirring so that the heat of reaction maintained the mixture at 140° C. After addition of all the dimethylketoxime the conversion was carried to completion by heating to 140° C. for another hour.

| | |
|---|---|
| Free NCO (%): | <0.6 |
| Blocked NCO (%): | 15.33 |
| Melting temperature: | 108–112° C. |
| Decomposition Temperature: | ~160° C. |
| Glass Transition Temperature (DTA): | 79–91° C. |

Figure 4:
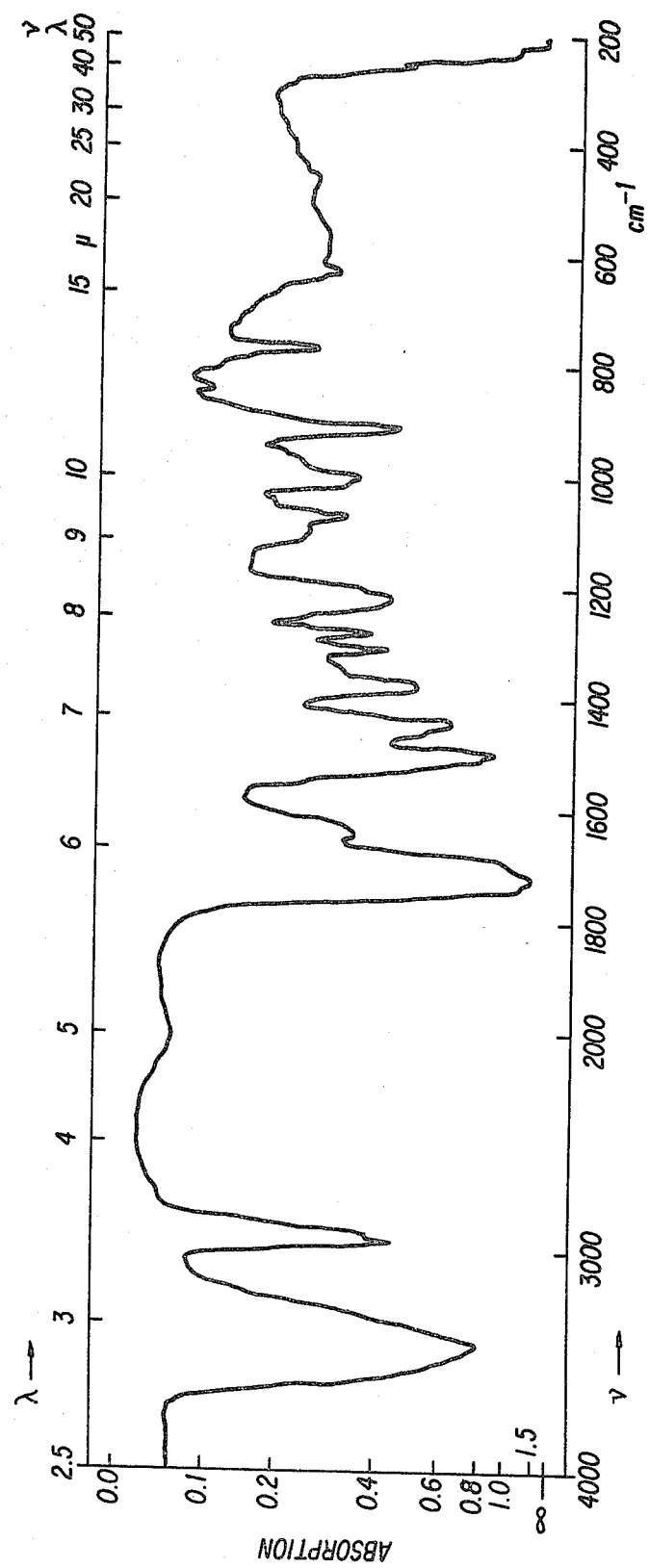
FIG. 4 shows the IR-spectrum of the reaction product from Example 4B.

The IR-spectrum of the reaction product is shown in FIG. 4.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A method for the production of a blocked isocyanate- and isocyanurate group-containing mixtures which comprises:
   reacting a monomeric cycloaliphatic polyisocyanate to form an intermediate mixture comprising an isocyanurate containing at least two free isocyanate groups; and
   blocking said intermediate isocyanurate mixture with dimethylketoxime at 50°–120° C.;
   wherein the amount of said dimethylketoxime is such that one equivalent of NCO group reacts with one equivalent of said dimethylketoxime.

2. The method of claim 1, wherein said polyisocyanate is a diisocyanate.

3. The method of claim 2, wherein said diisocyanate is selected from the group consisting of cyclobutane-1,2-diisocyanate, cyclohexane-1,3- and 1,4-diisocyanate, 3-isocyanato methyl-3,5,5-trimethylcyclohexylisocyanate, hexahydro-1,2-phenylene-diisocyanate, hexahydro-1,4-phenylenediisocyanate, 2,4- and 2,6-hexahydrotoluylenediisocyanate, perhydro-2,4' and 4,4'-diphenylmethanediisocyanate, and mixtures thereof.

4. The method of claim 3, wherein said diisocyanate is selected from the group consisting of 3-isocyanato methyl-3,5,5-trimethyl-cyclohexylisocyanate, 2,4-hexahydrotoluylenediisocyanate, 2,6-hexahydrotoluylenediisocyanate, perhydro-2,4'-diphenylmethanediisocyanate, perhydro-4,4'-diphenylmethanediisocyanate, and mixtures thereof.

5. The method of claim 4, wherein said diisocyanate is 3-isocyanatomethyl-3,5,5-trimethyl-cyclohexylisocyanate.

6. The method of claim 1, wherein the transformation of said monomeric polyisocyanate into said intermediate mixture is carried out in the presence of a catalyst.

7. The method of claim 6, wherein said catalyst is selected from the group consisting of metal naphthenates, sodium benzoate in dimethylformamide, alkaline earth-acetates, -formates, -carbonates, metal alkoxides, aluminum trichloride, iron acetylacetonate and a system comprising N,N'-endoethylenepiperazine and propylene oxide.

8. The method of claim 1, wherein the blocking reaction with said dimethylketoxime is carried out at 80°–120° C.

9. The method of claim 1, wherein said blocking reaction with dimethylketoxime is carried out in the presence of 0.001 to 1% of a catalyst.

10. The method of claim 9, wherein said catalyst is tin(II)-octanoate.

11. A mixture containing isocyanurate and isocyanate groups which comprises:
   at least 10% by weight of a cycloaliphatic isocyanurate containing at least two isocyanate groups blocked with dimethyl ketoxime; and
   a monomeric polyisocyanate blocked with dimethyl ketoxime in such amounts as necessary to complete 100% by weight of said mixture;

wherein the unblocked NCO-group content of said monomeric polyisocyanate is less than 0.5% by weight; and wherein said isocyanurate is substantially free of products which have more than three monomeric polyisocyanate units isocyanurate.

12. A mixture containing isocyanurate and blocked isocyanate groups which comprises:

at least 10% by weight of a cycloaliphatic isocyanurate containing at least two isocyanate groups blocked with dimethylketoxime; and a monomeric polyisocyanate blocked with dimethylketoxime in such amounts as necessary to complete 100% by weight of said mixture; and wherein the unblocked NCO-group content of said monomeric polyisocyanate is less than 0.5% by weight.

13. The mixture of claims 11 or 12, wherein said monomeric polyisocyanate is identical with the polyisocyanate used for the preparation of said isocyanurate.

14. The mixture of claims 11 or 12, wherein said polyisocyanate is a diisocyanate.

15. The mixture of claim 14, wherein said diisocyanate is selected from the group consisting of cyclobutane-1,2-diisocyanate, cyclohexane-1,3 and 1,4-diisocyanate, 3-isocyanatomethyl-3,5,5-trimethylcyclohexylisocyanate, hexahydro-1,2-phenylene-diisocyanate, hexahydro-1,4-phenylenediisocyanate, 2,4- and 2,6-hexahydrotoluylenediisocyanate, perhydro-2,4'-and 4,4'-diphenylmethanediisocyanate, and mixtures thereof.

16. The mixture of claim 15, wherein said diisocyanate is selected from the group consisting of 3-isocyanatomethyl-3,5,5-trimethyl-cyclohexylisocyanate, 2,4-hexahydrotoluylenediisocyanate, 2,6-hexahydrotoluylenediisocyanate, perhydro-2,4'-diphenylmethanediisocyanate, perhydro-4,4'-diphenylmethanediisocyanate, and mixtures thereof.

17. The mixture of claim 16, wherein said diisocyanate is 3-isocyanatomethyl-3,5,5-trimethylcyclohexylisocyanate.

* * * * *

UNITED STATES PATENT AND TRADEMARK OFFICE
CERTIFICATE OF CORRECTION

PATENT NO. : 4,306,051
DATED : Dec. 15, 1981
INVENTOR(S) : Rainer Gras, et. al.

It is certified that error appears in the above—identified patent and that said Letters Patent is hereby corrected as shown below:

Please correct the Priority Data to read as follows:

[30]---Foreign Application Priority Data

Jul. 20, 1977 [DE]  Fed. Rep. of Germany........2732662

Signed and Sealed this

Twenty-third Day of March 1982

|SEAL|

*Attest:*

*Attesting Officer*

GERALD J. MOSSINGHOFF

*Commissioner of Patents and Trademarks*